(12) United States Patent
Trail et al.

(10) Patent No.: US 11,318,329 B1
(45) Date of Patent: May 3, 2022

(54) IMAGING AND TREATMENT BEAM ENERGY MODULATION UTILIZING AN ENERGY ADJUSTER

(71) Applicant: ACCURAY INCORPORATED, Sunnyvale, CA (US)

(72) Inventors: Mark Trail, Sunnyvale, CA (US); Steve Vanderet, Sunnyvale, CA (US); Calvin R. Maurer, San Jose, CA (US); Daniel Gagnon, Sunnyvale, CA (US)

(73) Assignee: Accuray Incorporated, Sunnyvale, CA (US)

( * ) Notice: Subject to any disclaimer, the term of this patent is extended or adjusted under 35 U.S.C. 154(b) by 0 days.

(21) Appl. No.: 17/379,020

(22) Filed: Jul. 19, 2021

(51) Int. Cl.
*A61N 5/10* (2006.01)

(52) U.S. Cl.
CPC ......... *A61N 5/1081* (2013.01); *A61N 5/1031* (2013.01); *A61N 5/1042* (2013.01); *A61N 5/1048* (2013.01); *A61N 5/1083* (2013.01)

(58) Field of Classification Search
CPC ........ A61N 5/10; A61N 5/103; A61N 5/1031; A61N 5/1042; A61N 5/1048; A61N 5/1064; A61N 5/1065; A61N 5/1067; A61N 5/1077; A61N 5/1081–1084; A61N 2005/1091; A61N 2005/1092; A61B 6/06; A61B 6/405; A61B 6/48; A61B 6/4806; A61B 6/50; A61B 6/54; A61B 34/10; A61B 34/20; A61B 2034/107; A61B 2560/02; A61B 2560/0204; A61B 2560/0214; A61B 2560/0266; H01J 1/46; H01J 1/50; H01J 1/88; H01J 3/08; H01J 3/14; H01J 3/26; H01J 7/44; H01J 9/236; H01J 21/18; H01J 25/02; H01J 25/10; H01J 25/20; H01J 25/50; H01J 29/46; H01J 29/465; H01J 29/58; H01J 29/62; H01J 29/70; H01J 29/72; H01J 35/02; H01J 35/025; H01J 35/04; H01J 35/045; H01J 35/06; H01J 35/14; H01J 37/02; H01J 37/04; H01J 37/06; H01J 37/061; H01J 37/10; H01J 37/12; H01J 37/14; H01J 37/145; H01J 37/147; H01J 37/1471; H01J 37/1472; H01J 37/24; H01J 37/241; H01J 37/243; H01J 37/248; H01J 37/302; H01J 37/3023; H01J 37/3026; H01J 43/04; H01J 43/045;
(Continued)

(56) References Cited

U.S. PATENT DOCUMENTS

| 4,527,091 | A | * | 7/1985 | Preist | H01J 23/065 |
| | | | | | 313/293 |
| 4,969,170 | A | * | 11/1990 | Kikuchi | A61B 6/102 |
| | | | | | 378/114 |

(Continued)

*Primary Examiner* — Anastasia Midkiff
(74) *Attorney, Agent, or Firm* — Womble Bond Dickinson (US) LLP (57) ABSTRACT

Electromagnetic waves for an accelerating structure of the radiation delivery system are generated by a microwave source. The electromagnetic waves generated by the microwave source are adjusted by an energy adjuster to a first energy level. A kilovolt (kV) imaging beam is generated by the accelerating structure based on the first energy level. The electromagnetic waves generated by the magnetic source are adjusted by the energy adjuster to a second energy level. A megavolt (MV) treatment beam is generated by the accelerating structure based on the second energy level.

16 Claims, 9 Drawing Sheets

(58) Field of Classification Search
CPC .. H01J 43/06; H01J 43/08; H01J 43/14; H01J 2201/306; H01J 2201/34; H01J 2201/342; H01J 2203/02; H01J 2223/16; H01J 2223/18; H01J 2223/22; H01J 2225/02; H01J 2225/06; H01J 2225/10; H01J 2225/20; H01J 2225/50; H01J 2225/78; H01J 2229/58; H01J 2229/581; H01J 2229/582; H01J 2229/96; H01J 2229/964; H01J 2235/02; H01J 2235/06; H01J 2237/004; H01J 2237/04; H01J 2237/047; H01J 2237/0473; H01J 2237/15; H01J 2237/1501; H01J 2237/1504; H01J 2237/1508; H01J 2237/248; H01J 2237/2485; H01J 2237/2487; H02P 13/08; H02P 21/0003; H02P 21/0007; H02P 23/0004; H02P 23/0009
See application file for complete search history.

(56) References Cited

U.S. PATENT DOCUMENTS

| | | | |
|---|---|---|---|
| 8,143,816 B2 | 3/2012 | Clayton et al. | |
| 2001/0024117 A1* | 9/2001 | Kiyokawa | G01R 31/2603 324/76.49 |
| 2007/0236300 A1 | 10/2007 | Meddaugh et al. | |
| 2010/0121318 A1* | 5/2010 | Hancock | A61N 5/02 606/33 |
| 2016/0148773 A1* | 5/2016 | Einat | H01J 1/30 313/446 |
| 2018/0277276 A1* | 9/2018 | Purwar | G21K 5/04 |

* cited by examiner

IMAGING AND TREATMENT BEAM ENERGY MODULATION UTILIZING AN ENERGY ADJUSTER

TECHNICAL FIELD

The present disclosure relates to imaging and treatment beam energy modulation utilizing an energy adjuster.

BACKGROUND

In radiation treatment, a radiation delivery system may utilize a therapeutic radiation source to generate a treatment beam that provides a therapeutic dose of radiation to a target, such as a tumor of a patient. The radiation source may also operate in a mode that delivers a diagnostic imaging beam for the purposes of patient tumor imaging.

BRIEF DESCRIPTION OF THE DRAWINGS

The present disclosure will be understood more fully from the detailed description given below and from the accompanying drawings of various implementations of the disclosure.

DETAILED DESCRIPTION

Described herein are embodiments for using an energy adjuster to modulate electromagnetic waves of a radiation delivery system. The radiation delivery system may utilize a single radiation source that is capable of producing both imaging beams (also referred to as "diagnostic beams" hereafter) and treatment beams (also referred to as "therapeutic beams" hereafter) at different energy levels.

In a conventional radiation delivery system, a therapeutic radiation source is used to generate a treatment beam that provides a therapeutic dose of radiation to a target, such as a tumor of a patient. For example, the therapeutic radiation source may generate a megavolt (MV) treatment beam. The conventional radiation delivery system also includes an imaging radiation source that is used to generate an imaging beam to acquire imaging data associated with the target. For example, the X-ray radiation source may generate a kilovolt (kV) imaging beam. Thus, in order to provide a therapeutic dose of radiation to the target using a treatment beam, and to acquire imaging data associated with the target using an imaging beam, the conventional radiation delivery system is required to have two separate radiation sources (e.g., the therapeutic radiation source and the imaging radiation source), increasing the cost of a conventional radiation delivery system.

Aspects of the disclosure may remedy the above and other deficiencies by having a radiation delivery system that utilizes an energy adjuster to modulate electromagnetic waves of a radiation delivery system, such that a single radiation source is capable of producing both imaging and treatment beams. The radiation delivery system may include a microwave source, such as a magnetron or klystron, which generates electromagnetic waves. The energy adjuster may be operatively coupled to the microwave source and may receive the electromagnetic waves from the microwave source and modulate the electromagnetic waves to correspond to the energy level of an imaging beam or a treatment beam. The energy adjuster may modulate the electromagnetic waves to correspond to these energy levels without having to adjust the power of the microwave source.

The energy adjuster may be a mechanical or electromechanical assembly that is configured to modulate an electromagnetic wave. In embodiments, the energy adjuster may include a power variator. The power variator may include two loads, a circulator, a junction, and a sliding short. In some embodiments, the junction may be one of a Y-junction or a T-junction. In embodiments, the sliding short may be a conventional mechanical sliding short or an electromagnetic design that can rapidly produce changes in short-circuit position through the use of magnetically biased ferrites.

The radiation delivery system may further include an accelerating structure that may be operatively coupled to the energy adjuster to receive the modulated electromagnetic waves. The accelerating structure may accelerate the electron beam towards a radiation-emitting target (also referred to as "X-ray target" hereafter) to produce a treatment beam and/or imaging beam. In some embodiments, the radiation delivery system may include an apparatus that includes multiple radiation-emitting targets, as will be described in further detail below.

The radiation delivery system may also include a control system that is operatively coupled to the microwave source, the energy adjuster, and the accelerating structure. The control system may include a processing device and the processing logic of the processing device may cause the modulation of the electromagnetic waves by the energy adjuster, which causes the accelerating structure to generate the imaging beam and the treatment beam.

By utilizing an energy adjuster to modulate the electromagnetic waves to produce both imaging beams and treatment beams, the radiation delivery system is no longer required to include both a therapeutic radiation source to generate a treatment beam and an imaging radiation source to generate an imaging beam. Rather, a single radiation source may be used to generate both the treatment beam and the imaging beam, reducing the cost of the radiation delivery system and improving the performance of the radiation delivery system.

Figure 1A:
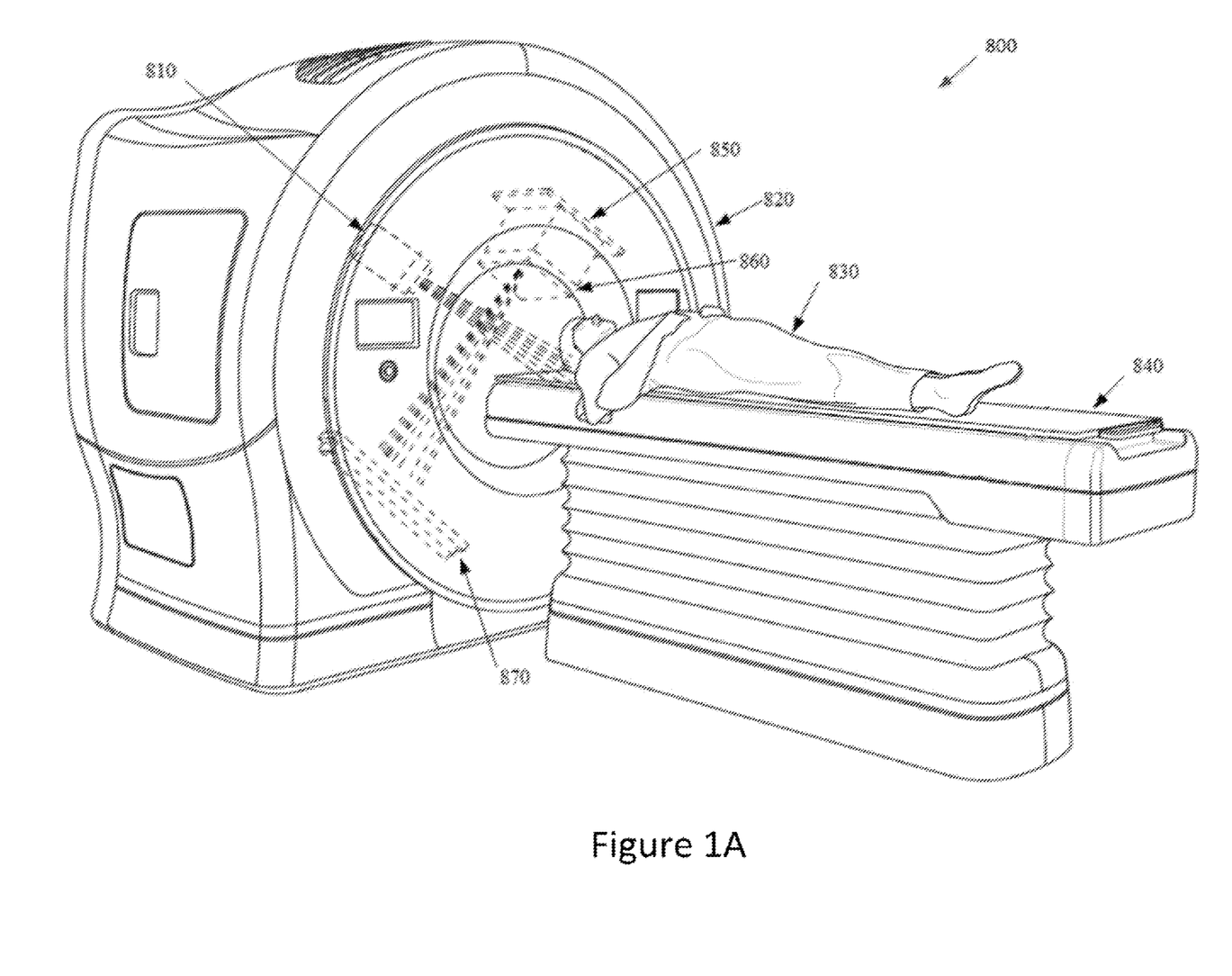
FIG. 1A illustrates a helical radiation delivery system, in accordance with embodiments described herein.

FIG. 1A illustrates a helical radiation delivery system 800 in accordance with embodiments of the present disclosure. The helical radiation delivery system 800 may include a linear accelerator (LINAC) 850 mounted to a ring gantry 820. The LINAC 850 may be used to generate a radiation beam (i.e., treatment beam) by directing an electron beam towards an x-ray emitting target. The treatment beam may deliver radiation to a target region (i.e., a tumor). The treatment system further includes a multileaf collimator (MLC) 860 coupled with the distal end of the LINAC 850. The MLC includes a housing that houses multiple leaves that are movable to adjust an aperture of the MLC to enable shaping of the treatment beam. In embodiments, the MLC 860 may be a binary MLC that includes a plurality of leaves arranged in two opposing banks, where the leaves of the two opposing banks are interdigitated with one another and can be opened or closed to form an aperture. In some embodiments, the MLC 860 may be an electromagnetically-actuated MLC. In embodiments, MLC 860 may be any other type of MLC. The ring gantry 820 has a toroidal shape in which the patient 830 extends through a bore of the ring/toroid and the LINAC 850 is mounted on the perimeter of the ring and rotates about the axis passing through the center to irradiate a target region with beams delivered from one or more angles around the patient. During treatment, the patient 830 may be simultaneously moved through the bore of the gantry on a treatment couch 840.

The helical radiation delivery system 800 includes an imaging system, comprising the LINAC 850 as an imaging source and an x-ray detector 870. The LINAC 850 may be used to generate a mega-voltage x-ray image (MVCT) of a region of interest (ROI) of patient 830 by directing a sequence of x-ray beams at the ROI which are incident on the x-ray detector 870 opposite the LINAC 850 to image the patient 830 for setup and generate pre-treatment images. In one embodiment, the helical radiation delivery system 800 may also include a secondary imaging system consisting of a kV imaging source 810 mounted orthogonally relative to the LINAC 850 (e.g., separated by 90 degrees) on the ring gantry 820 and may be aligned to project an imaging x-ray beam at a target region and to illuminate an imaging plane of a detector after passing through the patient 130.

Figure 1B:
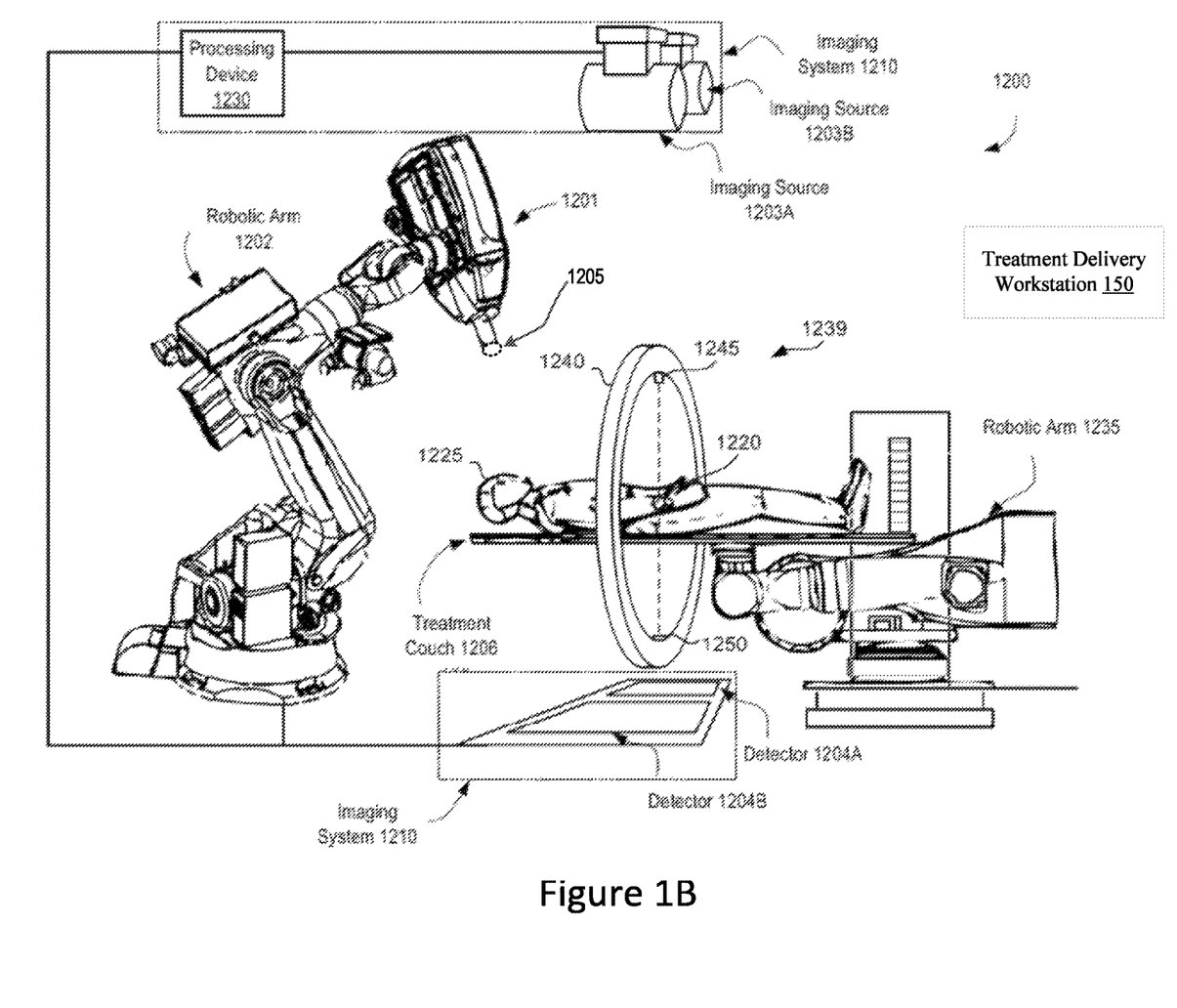
FIG. 1B illustrates a robotic radiation treatment system that may be used in accordance with embodiments described herein.

FIG. 1B illustrates a radiation treatment system 1200 that may be used in accordance with alternative embodiments described herein. As shown, FIG. 1B illustrates a configuration of a radiation treatment system 1200. In the illustrated embodiments, the radiation treatment system 1200 includes a linear accelerator (LINAC) 1201 that acts as a radiation treatment source and an MLC 1205 coupled with the distal end of the LINAC 1201 to shape the treatment beam. In one embodiment, the LINAC 1201 is mounted on the end of a robotic arm 1202 having multiple (e.g., 5 or more) degrees of freedom in order to position the LINAC 1201 to irradiate a pathological anatomy (e.g., target) with beams delivered from many angles, in many planes, in an operating volume around a patient. Treatment may involve beam paths with a single isocenter, multiple isocenters, or with a non-isocentric approach.

LINAC 1201 may be positioned at multiple different nodes (predefined positions at which the LINAC 1201 is stopped and radiation may be delivered) during treatment by moving the robotic arm 1202. At the nodes, the LINAC 1201 can deliver one or more radiation treatment beams to a target, where the radiation beam shape is determined by the leaf positions in the MLC 1205. The nodes may be arranged in an approximately spherical distribution about a patient. The particular number of nodes and the number of treatment beams applied at each node may vary as a function of the location and type of pathological anatomy to be treated.

In another embodiment, the robotic arm 1202 and LINAC 1201 at its end may be in continuous motion between nodes while radiation is being delivered. The radiation beam shape and 2-D intensity map is determined by rapid motion of the leaves in the MLC 1205 during the continuous motion of the LINAC 1201.

In some embodiments, the radiation treatment system 1200 may include an imaging system 1210 having a processing device 1230 connected with x-ray sources 1203A and 1203B (i.e., imaging sources) and fixed x-ray detectors 1204A and 1204B. The imaging system 1210 may be utilized to generate additional imaging beams. Alternatively, the x-ray sources 1203A, 1203B and/or x-ray detectors 1204A, 1204B may be mobile, in which case they may be repositioned to maintain alignment with the target, or alternatively to image the target from different orientations or to acquire many x-ray images and reconstruct a three-dimensional (3D) cone-beam CT. In one embodiment, LINAC 1201 serves as an imaging source, where the LINAC power level is reduced to acceptable levels for imaging.

Imaging system 1210 may perform computed tomography (CT) such as cone beam CT or helical megavoltage computed tomography (MVCT), and images generated by imaging system 1210 may be two-dimensional (2D) or three-dimensional (3D). The two x-ray sources 1203A and 1203B may be mounted in fixed positions on the ceiling of an operating room and may be aligned to project x-ray imaging beams from two different angular positions (e.g., separated by 90 degrees) to intersect at a machine isocenter (referred to herein as a treatment center, which provides a reference point for positioning the patient on a treatment couch 1206, having a robotic arm 1235, during treatment) and to illuminate imaging planes of respective detectors 1204A and 1204B after passing through the patient. In one embodiment, imaging system 1210 provides stereoscopic imaging of a target and the surrounding volume of interest (VOI). In other embodiments, imaging system 1210 may include more or less than two x-ray sources and more or less than two detectors, and any of the detectors may be movable rather than fixed. In yet other embodiments, the positions of the x-ray sources and the detectors may be interchanged. Detectors 1204A and 1204B may be fabricated from a scintillating material that converts the x-rays to visible light (e.g., amorphous silicon), and an array of CMOS (complementary metal oxide silicon) or CCD (charge-coupled device) imaging cells that convert the light to a digital image that can be compared with a reference image during an image registration process that transforms a coordinate system of the digital image to a coordinate system of the reference image, as is well known to the skilled artisan. The reference image may be, for example, a digitally reconstructed radiograph (DRR), which is a virtual x-ray image that is generated from a 3D CT image based on simulating the x-ray image formation process by casting rays through the CT image.

In one embodiment, IGRT delivery system 1200 also includes a secondary imaging system 1239. Imaging system 1239 may be a Cone Beam Computed Tomography (CBCT) imaging system. Alternatively, other types of volumetric imaging systems may be used. The secondary imaging system 1239 includes a rotatable gantry 1240 (e.g., a ring) attached to an arm and rail system (not shown) that move the rotatable gantry 1240 along one or more axes (e.g., along an axis 1220 that extends from a head to a foot of the treatment couch 1206. An imaging source 1245 and a detector 1250 are mounted to the rotatable gantry 1240. The rotatable gantry 1240 may rotate 360 degrees about the axis that extends from the head to the foot of the treatment couch.

As shown in FIG. 1B, the image-guided radiation treatment system 1200 may further be associated with a treatment delivery workstation 150. The treatment delivery workstation may be remotely located from the radiation treatment system 1200 in a different room than the treatment room in which the radiation treatment system 1200 and patient are located. The treatment delivery workstation 150 may include a processing device (which may be processing device 1230 or another processing device) and memory that modify a treatment delivery to the patient 1225 based on a detection of a target motion that is based on one or more image registrations, as described herein.

Figure 1C:
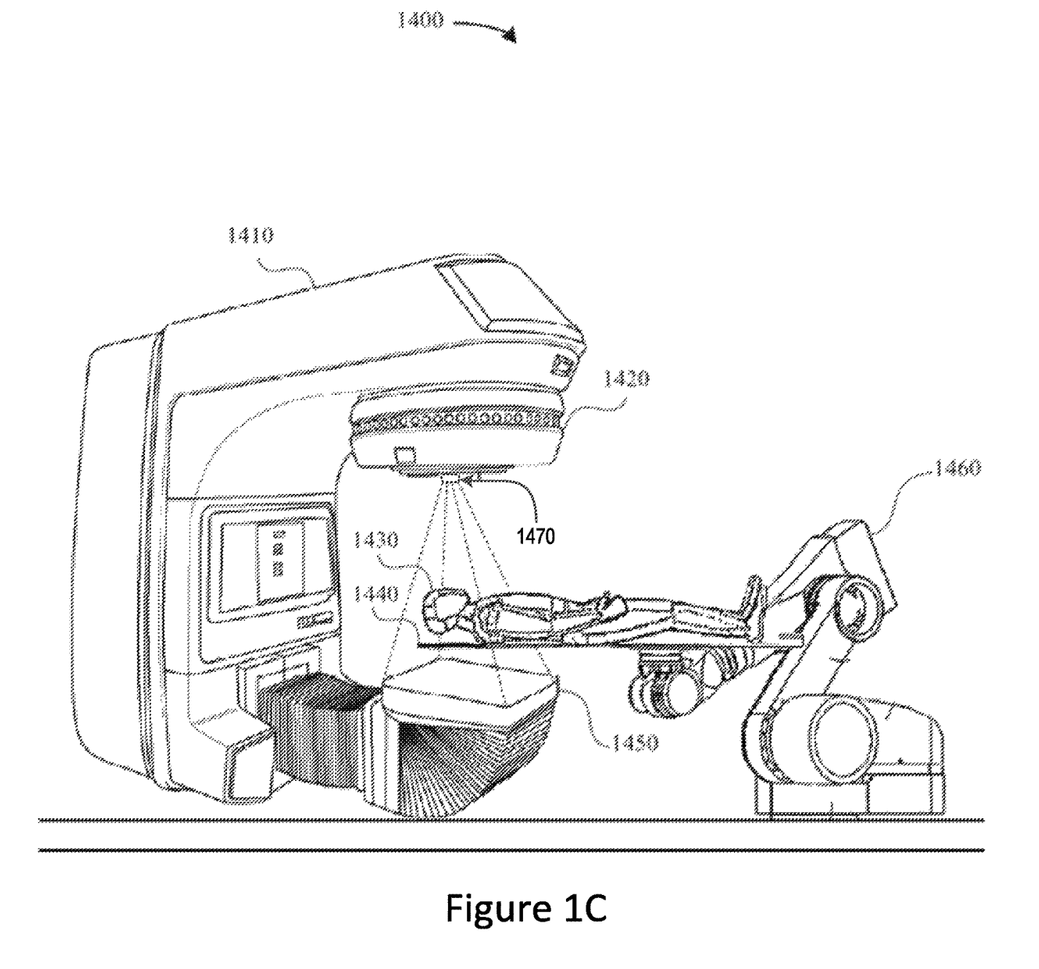
FIG. 1C illustrates a C-arm gantry-based radiation treatment system, in accordance with embodiments described herein.

FIG. 1C illustrates a C-arm radiation delivery system 1400. In one embodiment, in the C-arm system 1400 the beam energy of a LINAC may be adjusted during treatment and may allow the LINAC to be used for both x-ray imaging and radiation treatment. In another embodiment, the system 1400 may include an onboard kV imaging system to generate x-ray images and a separate LINAC to generate the higher energy therapeutic radiation beams. The system 1400 includes a C-arm gantry 1410, a LINAC 1420, an MLC 1470 coupled with the distal end of the LINAC 1420 to shape the beam, and a portal imaging detector 1450. The C-arm gantry 1410 may be rotated to an angle corresponding to a selected projection and used to acquire an x-ray image of a VOI of a patient 1430 on a treatment couch 1440 coupled to a robotic arm 1460. In embodiments that include a portal imaging system, the LINAC 1420 may generate an x-ray beam that passes through the target of the patient 1430 and are incident on the portal imaging detector 1450, creating an x-ray image of the target. After the x-ray image of the target has been generated, the beam energy of the LINAC 1420 may be increased so the LINAC 1420 may generate a radiation beam to treat a target region of the patient 1430. In another embodiment, the kV imaging system may generate an x-ray beam that passes through the target of the patient 1430, creating an x-ray image of the target. In some embodiments, the portal imaging system may acquire portal images during the delivery of a treatment. The portal imaging detector 1450 may measure the exit radiation fluence after the beam passes through the patient 1430. This may enable internal or external fiducials or pieces of anatomy (e.g., a tumor or bone) to be localized within the portal images.

Alternatively, the kV imaging source or portal imager and methods of operations described herein may be used with yet other types of gantry-based systems. In some gantry-based systems, the gantry rotates the kV imaging source and LINAC around an axis passing through the isocenter. Gantry-based systems include ring gantries having generally toroidal shapes in which the patient's body extends through the bore of the ring/toroid, and the kV imaging source and LINAC are mounted on the perimeter of the ring and rotates about the axis passing through the isocenter. Gantry-based systems may further include C-arm gantries, in which the kV imaging source and LINAC are mounted, in a cantilever-like manner, over and rotates about the axis passing through the isocenter. In another embodiment, the kV imaging source and LINAC may be used in a robotic arm-based system, which includes a robotic arm to which the kV imaging source and LINAC are mounted as discussed above. Aspects of the present disclosure may further be used in other such systems such as a gantry-based LINAC system, static imaging systems associated with radiation therapy and radiosurgery, proton therapy systems using an integrated image guidance, interventional radiology and intraoperative x-ray imaging systems, etc.

Figure 2:
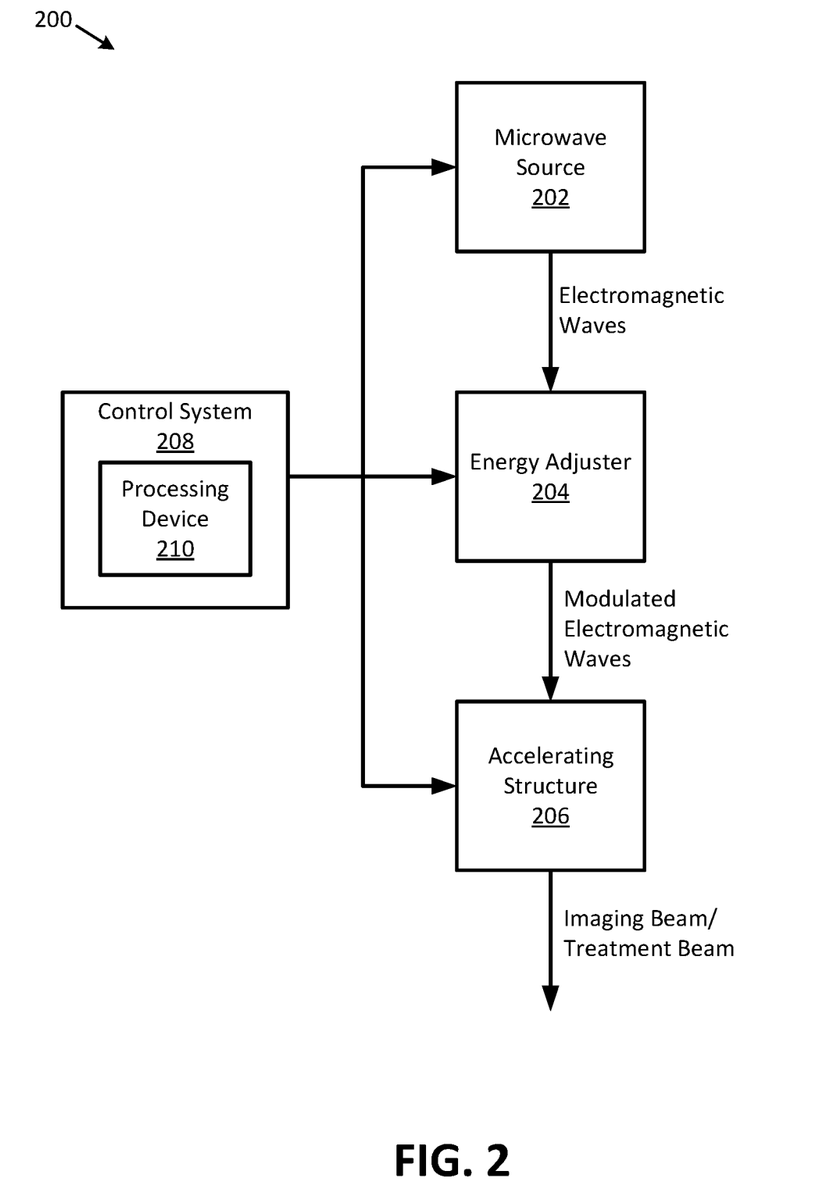
FIG. 2 is an illustration of an example of radiation delivery system utilizing an energy adjuster to modulate electromagnetic waves to generate imaging beams and treatment beams, in accordance with embodiments of the disclosure.

FIG. 2 is an illustration of an example of radiation delivery system 200 utilizing an energy adjuster to modulate electromagnetic waves to generate imaging beams and treatment beams, in accordance with embodiments of the disclosure. In embodiments, the radiation delivery system 200 may correspond to, and include the components of, one of the radiation delivery systems previously described at FIGS. 1A-C.

The radiation delivery system 200 includes a microwave source 202 that generates electromagnetic waves. In some embodiments, the microwave source 202 may be a magnetron. In embodiments, the microwave source 202 may be a klystron. In an embodiment, the microwave source 202 may be any other type of component capable of generating electromagnetic waves.

The radiation delivery system 200 may include an energy adjuster 204 that is operatively coupled to the microwave source 202. The energy adjuster 204 may modulate the electromagnetic waves that are received from microwave source 202. The energy adjuster 204 may be a mechanical or electromechanical assembly that is configured to modulate an electromagnetic wave. As previously described, the energy adjuster 204 may modulate the energy level of the electromagnetic wave to correspond to an imaging beam, such as a kV imaging beam, or a treatment beam, such as an MV treatment beam. In embodiments, the energy adjuster may include a power variator, which will be described in additional detail at FIGS. 3A and 3B below. In embodiments, the energy adjuster 204 may be able to vary the power level of the electromagnetic waves from 0-100% of the power of microwave source 202. In some embodiments, the energy adjuster 204 may be used to dynamically adjust the electromagnetic waves over the range of power levels during a radiation treatment session.

The radiation delivery system 200 may include an accelerating structure 206 that may be operatively coupled to the energy adjuster 204 to receive the modulated electromagnetic waves. The accelerating structure may utilize the modulated electromagnetic waves to accelerate an electron beam towards an X-ray target (not shown) to produce a variety of treatment beams and/or imaging beams, as previously described.

The radiation delivery system 200 may include a control system 208 that is operatively coupled to the microwave source 202, the energy adjuster 204, and the accelerating structure 206. The control system 208 may include a processing device 210 that includes processing logic that controls the microwave source 202, the energy adjuster 204, and the accelerating structure 206. In embodiments, processing device 210 may be provided by one or more general-purpose processing devices such as a microprocessor, central processing unit, or the like. In an illustrative example, processing device 210 may include a complex instruction set computing (CISC) microprocessor, reduced instruction set computing (RISC) microprocessor, very long instruction word (VLIW) microprocessor, or a processor implementing other instruction sets or processors implementing a combination of instruction sets. Processing device 210 may also comprise one or more special-purpose processing devices such as an application specific integrated circuit (ASIC), a field programmable gate array (FPGA), a digital signal processor (DSP), network processor, or the like.

Figure 3A:
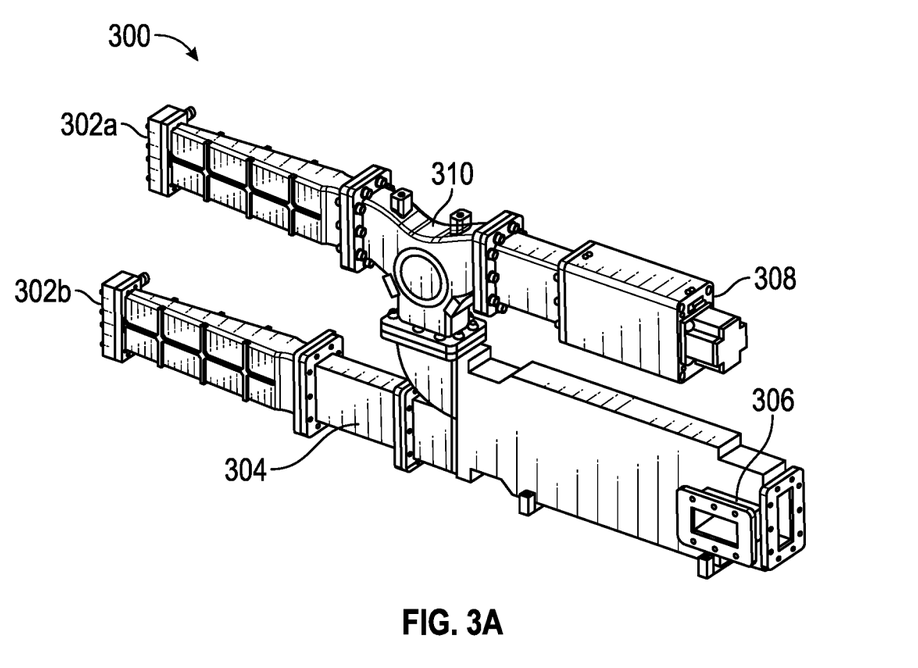
FIG. 3A is an illustration of an example of a power variator including a Y-junction, in accordance with embodiments of the disclosure.

FIG. 3A is an illustration of an example of a power variator 300 including a Y-junction, in accordance with embodiments of the disclosure. As previously described, the power variator 300 may be utilized to modulate electromagnetic waves to correspond to energy levels of imaging beams and treatment beams.

In embodiments, the power variator 300 may include load 302a, load 302b, phase wand 304, circulator 306, Y-junction 310, sliding short 308, or any combination thereof. The phase wand 304 may be placed at the load 302b to provide a reflection of a desired amplitude and phase. The circulator 306 may be a passive device that allows electromagnetic waves entering the circulator 306 to exit the port directly after the one it entered. In some embodiments, the circulator 306 may be a four-port circulator. In an embodiment, multiple circulators may be used.

The sliding short 308 may be a mechanical or electromechanical assembly which may be used to adjust a short-circuit position (e.g., electrical length) of the power variator 300, changing the power level of the electromagnetic waves provided to the accelerator structure. In some embodiments, the sliding short 308 may be an electromagnetically controlled short-circuit in which the phase length of the electromagnetic waves are controlled by the biasing of ferrite material. In embodiments, the sliding short 308 may be a mechanical sliding short in which a plunger is mechanically moved within the rectangular waveguide to control the phase length of the electromagnetic waves. In some embodiments, other types of sliding shorts 308 may be used.

The Y-junction 310 may be a junction that is operatively coupled to the circulator 306, load 302a, and sliding short 308. The Y-junction 310 may be a waveguide junction that guides the electromagnetic waves between these components of the power variator 300. The Y-junction 310 may include three ports that are each separated by a same or similar angle to form a "Y" shape.

Figure 3B:
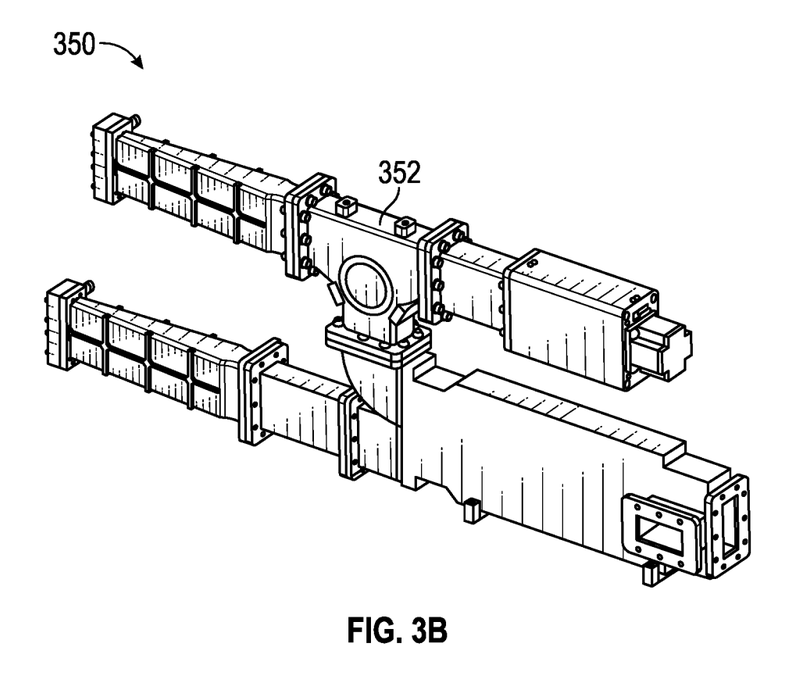
FIG. 3B is an illustration of an example of a power variator including a T-junction, in accordance with embodiments of the disclosure.

FIG. 3B is an illustration of an example of a power variator 350 including a T-junction, in accordance with embodiments of the disclosure. Power variator 350 may include similar components as power variator 300, as previously described at FIG. 3A. Power variator 350, however, includes a T-junction 352 rather than a Y-junction. The T-junction 352 may be a waveguide junction that guides the electromagnetic waves between the load, sliding short, and circulator, as previously described. The T-junction 352 may include three ports, in which two of the ports form an axis that is perpendicular to the third port to form a "T" shape.

It should be noted that the T-junction 352 and the Y-junction included in FIGS. 3A and 3B are shown for illustrative purposes only and are not meant to limit the disclosure. Embodiments of the disclosure may utilize Y-junctions and/or T-junctions that may have different appearances, geometries, or other properties than the Y-junction and T-junction illustrated in FIGS. 3A and 3B.

Figure 4A:
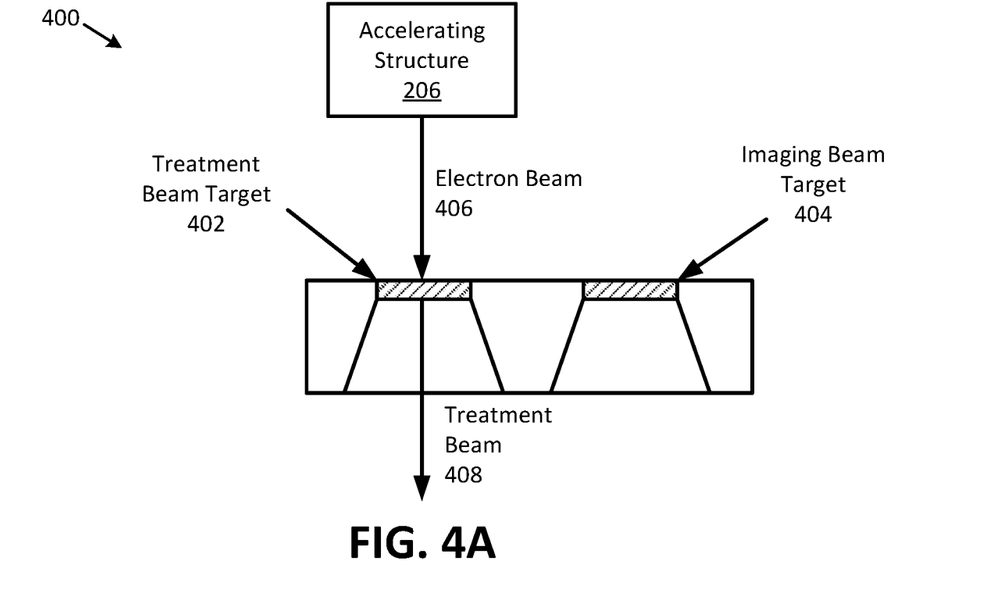
FIG. 4A is an illustration of an example of a multi X-ray target assembly that includes multiple, energy specific, radiation generating targets, in accordance with embodiments of the disclosure.

FIG. 4A is an example of a multi X-ray target assembly 400 that includes multiple, energy specific, radiation generating targets, in accordance with embodiments of the disclosure. In some embodiments, a radiation delivery system may include a multi X-ray target assembly 400 that includes multiple X-ray targets to maximize X-ray production yield for each treatment and imaging beam. The multi X-ray target assembly 400 may include a treatment beam target 402 and an imaging beam target 404. Although multi X-ray target assembly 400 is shown as having two X-ray targets, embodiments of the disclosure may include two or more X-ray targets in the multi X-ray target assembly 400. The different X-ray targets may be optimized for various beam energy levels that are included in a single assembly. The positioning of the multi X-ray target assembly 400 may be adjusted such that the modulated electromagnetic waves are accelerated towards the appropriate X-ray target based on the energy level of the modulated electromagnetic waves, as will be described in further detail below.

As previously described, to generate a treatment photon beam 408, the electron beams 406 may be accelerated by an accelerating structure 206 towards treatment beam target 402. Treatment beam target 402 may be formed of a material having a high atomic number, which causes the generation of treatment photon beam 408 when the electron beam 406 is accelerated into the treatment beam target 402. In embodiments, the electron beams 406 that are accelerated into the treatment beam target 402 may be modulated to an energy level that corresponds to treatment photon beam 408. For example, the electron beams 406 may be modulated to an energy level that corresponds to an MV treatment photon beam.

Figure 4B:
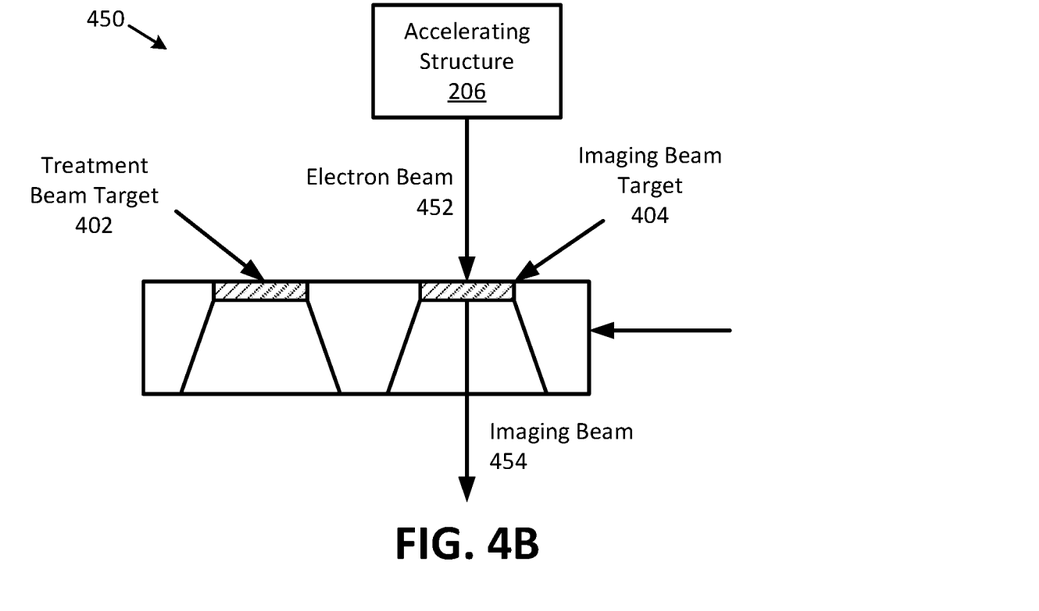
FIG. 4B is an illustration of an example of a multi X-ray target assembly being repositioned to cause treatment or imaging electron beams to impinge on the appropriate, energy specific radiation generating target, in accordance with embodiments of the disclosure.

FIG. 4B is an illustration of an example of a multi X-ray target assembly 450 being repositioned to cause treatment or imaging electron beams to impinge on the appropriate, energy specific radiation generating target, in accordance with embodiments of the disclosure. In FIG. 4B, accelerating structure 206 is accelerating a diagnostic energy-level electron beams 452 that have an energy level that corresponds to an imaging beam 454. Because the electron beams 452 have an energy level that corresponds to imaging beam 454, the multi X-ray target assembly 450 may be linearly translated to position the imaging beam target 404 in the path of the electron beams 452.

Imaging beam target 404 may be formed of a material having a low atomic number, which causes the generation of imaging photon beam 454 when the electron beams 452 are accelerated into the imaging beam target 404. In embodiments, the imaging beam target 404 may have a smaller thickness than the treatment beam target 402 to reduce the attenuation for the generated imaging beam 454.

Figure 5:
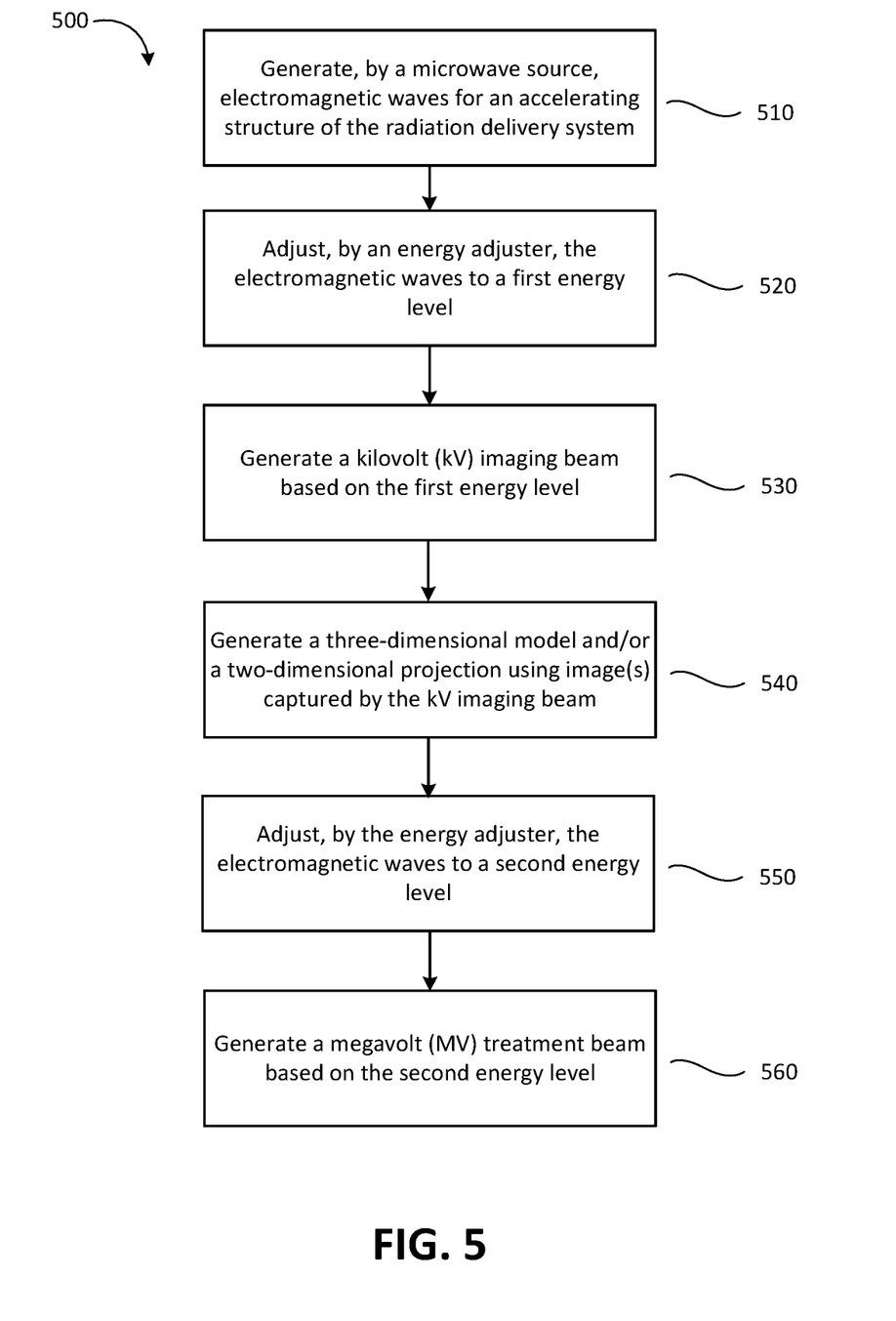
FIG. 5 depicts a flow diagram of a method of utilizing an energy adjuster to generate imaging and treatment beams, in accordance with embodiments of the disclosure.

FIG. 5 depicts a flow diagram of a method 500 of utilizing an energy adjuster to generate imaging and treatment beams, in accordance with embodiments of the disclosure. Method 500 may be performed, at least in part, by processing logic that may comprise hardware (e.g., circuitry, dedicated logic, programmable logic, a processor, a processing device, a central processing unit (CPU), a system-on-chip (SoC), etc.), software (e.g., instructions running/executing on a processing device), firmware (e.g., microcode), or a combination thereof. In embodiments, various portions of method 500 may be performed by one or more components of a radiation delivery system as previously described at FIGS. 1A-2.

With reference to FIG. 5, method 500 illustrates example functions used by various embodiments. Although specific function blocks ("blocks") are disclosed in method 500, such blocks are examples. That is, embodiments are well suited to performing various other blocks or variations of the blocks recited in method 500. It is appreciated that the blocks in method 500 may be performed in an order different than presented, and that not all of the blocks in method 500 may be performed.

Method 500 begins at block 510, where a microwave source generates electromagnetic waves for an accelerating structure of the radiation delivery system.

At block 520, an energy adjuster adjusts the electromagnetic waves to a first energy level. In embodiments, the first energy level may correspond to an energy level of an imaging beam.

At block 530, an accelerating structure generates a kilovolt (kV) imaging beam based on the first energy level. In some embodiments, the kV imaging beam may have an energy level between 50-1000 kV. In embodiments, the imaging beam may be an MV energy beam having an energy level that is greater than 1000 kV. In some embodiments, multiple imaging beams having different energy levels may be used.

At block 540, processing logic of a processing device generates a three-dimensional model and/or a two-dimensional projection using one or more images captured by the kV imaging beam. The processing logic may generate a three-dimensional model using two or more images that are captured by the kV imaging beam.

At block 550, the energy adjuster adjusts the electromagnetic waves to a second energy level. In embodiments, the second energy level may correspond to an energy level of a treatment beam.

At block 560, the accelerating structure generates a megavolt (MV) treatment beam based on the second energy level. In embodiments, the MV treatment beam may have an energy level between 1-20 MV. In some embodiments, multiple treatment beams having different energy levels may be used.

In embodiments, blocks 520-560 may be iteratively performed to interleave one or more imaging beams and one or more treatment beams during a treatment session. In some embodiments, blocks 520-560 may be performed during a single rotation of a gantry of a radiation delivery system. In embodiments, blocks 520-560 may be performed during multiple rotations in the case of helical reconstruction.

Figure 6:
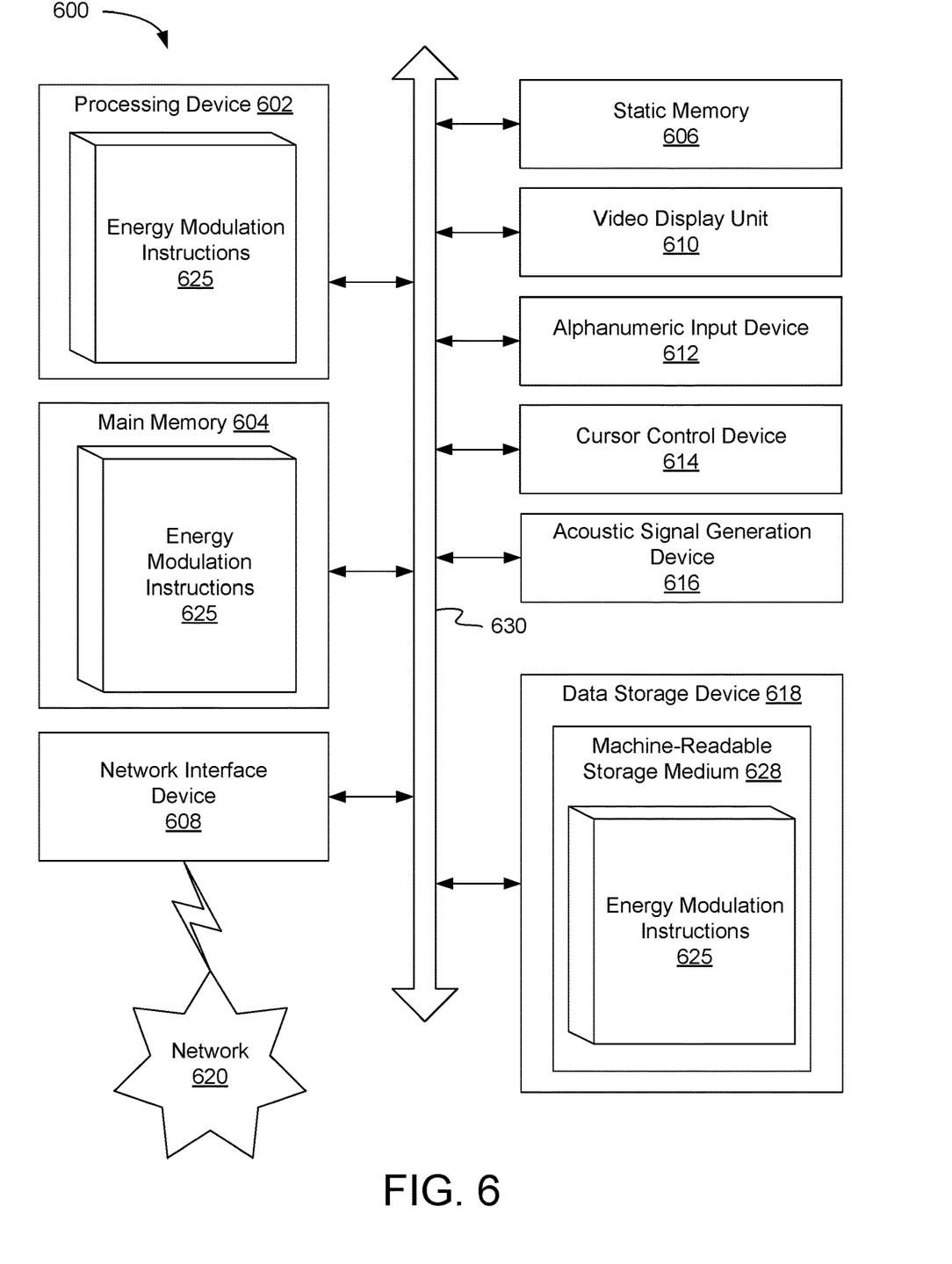
FIG. 6 is a block diagram of an example computing device that may perform one or more of the operations described herein, in accordance with some embodiments.

FIG. 6 is a block diagram of an example computing device 600 that may perform one or more of the operations described herein, in accordance with some embodiments. Computing device 600 may be connected to other computing devices in a LAN, an intranet, an extranet, and/or the Internet. The computing device may operate in the capacity of a server machine in client-server network environment or in the capacity of a client in a peer-to-peer network environment. The computing device may be provided by a personal computer (PC), a set-top box (STB), a server, a network router, switch or bridge, or any machine capable of executing a set of instructions (sequential or otherwise) that specify actions to be taken by that machine. Further, while only a single computing device is illustrated, the term "computing device" shall also be taken to include any collection of computing devices that individually or jointly execute a set (or multiple sets) of instructions to perform the methods discussed herein.

The example computing device 600 may include a processing device (e.g., a general purpose processor, a PLD, etc.) 602, a main memory 604 (e.g., synchronous dynamic random access memory (DRAM), read-only memory (ROM)), a static memory 606 (e.g., flash memory and a data storage device 618), which may communicate with each other via a bus 630.

Processing device 602 may be provided by one or more general-purpose processing devices such as a microprocessor, central processing unit, or the like. In an illustrative example, processing device 602 may comprise a complex instruction set computing (CISC) microprocessor, reduced instruction set computing (RISC) microprocessor, very long instruction word (VLIW) microprocessor, or a processor implementing other instruction sets or processors implementing a combination of instruction sets. Processing device 602 may also comprise one or more special-purpose processing devices such as an application specific integrated circuit (ASIC), a field programmable gate array (FPGA), a digital signal processor (DSP), network processor, or the like. The processing device 602 may be configured to execute the operations described herein, in accordance with one or more aspects of the present disclosure, for performing the operations and steps discussed herein.

Computing device 600 may further include a network interface device 608 which may communicate with a network 620. The computing device 600 also may include a video display unit 610 (e.g., a liquid crystal display (LCD) or a cathode ray tube (CRT)), an alphanumeric input device 612 (e.g., a keyboard), a cursor control device 614 (e.g., a mouse) and an acoustic signal generation device 616 (e.g., a speaker). In one embodiment, video display unit 610, alphanumeric input device 612, and cursor control device 614 may be combined into a single component or device (e.g., an LCD touch screen).

Data storage device 618 may include a computer-readable storage medium 628 on which may be stored one or more sets of instructions that may include energy modulation instructions 625 for carrying out the operations described herein, in accordance with one or more aspects of the present disclosure. The instructions may also reside, completely or at least partially, within main memory 604 and/or within processing device 602 during execution thereof by computing device 600, main memory 604 and processing device 602 also constituting computer-readable media. The instructions may further be transmitted or received over a network 620 via network interface device 608.

While computer-readable storage medium 628 is shown in an illustrative example to be a single medium, the term "computer-readable storage medium" should be taken to include a single medium or multiple media (e.g., a centralized or distributed database and/or associated caches and servers) that store the one or more sets of instructions. The term "computer-readable storage medium" shall also be taken to include any medium that is capable of storing, encoding or carrying a set of instructions for execution by the machine and that cause the machine to perform the methods described herein. The term "computer-readable storage medium" shall accordingly be taken to include, but not be limited to, solid-state memories, optical media and magnetic media.

It should be noted that the methods and apparatus described herein are not limited to use only with medical diagnostic imaging and treatment. In alternative implementations, the methods and apparatus herein may be used in applications outside of the medical technology field, such as industrial imaging and non-destructive testing of materials. In such applications, for example, "treatment" may refer generally to the effectuation of an operation controlled by the treatment planning system, such as the application of a beam (e.g., radiation, acoustic, etc.) and "target" may refer to a non-anatomical object or area.

The preceding description sets forth numerous specific details such as examples of specific systems, components, methods, and so forth, in order to provide a good understanding of several embodiments of the present disclosure. It will be apparent to one skilled in the art, however, that at least some embodiments of the present disclosure may be practiced without these specific details. In other instances, well-known components or methods are not described in detail or are presented in simple block diagram format in order to avoid unnecessarily obscuring the present disclosure. Thus, the specific details set forth are merely exemplary. Particular embodiments may vary from these exemplary details and still be contemplated to be within the scope of the present disclosure.

Reference throughout this specification to "one embodiment" or "an embodiment" means that a particular feature, structure, or characteristic described in connection with the embodiments included in at least one embodiment. Thus, the appearances of the phrase "in one embodiment" or "in an embodiment" in various places throughout this specification are not necessarily all referring to the same embodiment.

Although the operations of the methods herein are shown and described in a particular order, the order of the operations of each method may be altered so that certain operations may be performed in an inverse order or so that certain operation may be performed, at least in part, concurrently with other operations. In another embodiment, instructions or sub-operations of distinct operations may be in an intermittent or alternating manner.

The above description of illustrated implementations of the invention, including what is described in the Abstract, is not intended to be exhaustive or to limit the invention to the precise forms disclosed. While specific implementations of, and examples for, the invention are described herein for illustrative purposes, various equivalent modifications are possible within the scope of the invention, as those skilled in the relevant art will recognize. The words "example" or "exemplary" are used herein to mean serving as an example, instance, or illustration. Any aspect or design described herein as "example" or "exemplary" is not necessarily to be construed as preferred or advantageous over other aspects or designs. Rather, use of the words "example" or "exemplary" is intended to present concepts in a concrete fashion. As used in this application, the term "or" is intended to mean an inclusive "or" rather than an exclusive "or". That is, unless specified otherwise, or clear from context, "X includes A or B" is intended to mean any of the natural inclusive permutations. That is, if X includes A; X includes B; or X includes both A and B, then "X includes A or B" is satisfied under any of the foregoing instances. In addition, the articles "a" and "an" as used in this application and the appended claims should generally be construed to mean "one or more" unless specified otherwise or clear from context to be directed to a singular form. Moreover, use of the term "an embodiment" or "one embodiment" or "an implementation" or "one implementation" throughout is not intended to mean the same embodiment or implementation unless described as such. Furthermore, the terms "first," "second," "third," "fourth," etc. as used herein are meant as labels to distinguish among different elements and may not necessarily have an ordinal meaning according to their numerical designation.

What is claimed is:

1. A radiation delivery system, comprising:
    a linear accelerator (LINAC), comprising:
        a microwave source to generate electromagnetic waves;
        an energy adjuster operatively coupled to the microwave source, the energy adjuster to modulate the electromagnetic waves generated by the microwave source,
    wherein the energy adjuster comprises a power variator comprising a Y-junction;
        an accelerating structure operatively coupled to the energy adjuster, the accelerating structure to generate a kilovolt (kV) imaging beam and a megavolt (MV) treatment beam based on the modulated electromagnetic waves; and
        a control system operatively coupled to the microwave source, the energy adjuster and the accelerating structure, the control system to cause the modulation of the electromagnetic waves by the energy adjuster to cause the accelerating structure to generate the kV imaging beam and the MV treatment beam.

2. The radiation delivery system of claim 1, further comprising:
    a multi target X-ray target assembly comprising a first target for the kV imaging beam and a second target for the MV treatment beam.

3. The radiation delivery system of claim 1, further comprising:
    a processing device to generate a two-dimensional projection using the kV imaging beam.

4. The radiation delivery system of claim 1, further comprising:
    a processing device to generate a three-dimensional model using a plurality of two-dimensional images captured using the kV imaging beam.

5. The radiation delivery system of claim 1, wherein the kV imaging beam and the MV treatment beam are delivered during one or more rotations of a gantry.

6. The radiation delivery system of claim 5, wherein the gantry comprises one of a ring gantry, a C-arm gantry, or a robotic arm.

7. The radiation delivery system of claim 1, wherein the kV imaging beam and the MV treatment beam are interleaved.

8. The radiation delivery system of claim 1, wherein the kV imaging beam has a first energy level between 50-1,000 kV and wherein the MV treatment beam has a second energy level between 1-20 MV.

9. A method of controlling a radiation delivery system, the method comprising:
    generating, by a microwave source of the radiation delivery system, electromagnetic waves for an accelerating structure of the radiation delivery system;
    adjusting, by an energy adjuster of the radiation delivery system, the electromagnetic waves generated by the microwave source to a first energy level wherein the energy adjuster comprises a power variator comprising a Y-junction;
    generating, by the accelerating structure, a kilovolt (kV) imaging beam based on the first energy level;
    adjusting, by the energy adjuster, the electromagnetic waves generated by the microwave source to a second energy level; and
    generating, by the accelerating structure, a megavolt (MV) treatment beam based on the second energy level.

10. The method of claim 9, wherein the electromagnetic waves generated by the microwave source are dynamically adjusted by the energy adjuster during a treatment session.

11. The method of claim 9, further comprising:
    generating, by a processing device, a three-dimensional model using a plurality of two-dimensional images captured using the kV imaging beam.

12. The method of claim 9, wherein the kV imaging beam and the MV treatment beam are delivered during one or more rotations of a gantry.

13. A non-transitory computer-readable storage medium including instructions which, when executed by a processing device of a radiation delivery system, cause the radiation delivery system to:

generate, by a microwave source of the radiation delivery system, electromagnetic waves for an accelerating structure of the radiation delivery system;

adjust, by an energy adjuster of the radiation delivery system, the electromagnetic waves generated by the microwave source to a first energy level wherein the energy adjuster comprises a power variator comprising a Y-junction;

generate, by the accelerating structure, a kilovolt (kV) imaging beam based on the first energy level;

adjust, by the energy adjuster, the electromagnetic waves generated by the microwave source to a second energy level; and generate, by the accelerating structure, a megavolt (MV) treatment beam based on the second energy level.

14. The non-transitory computer-readable storage medium of claim 13, wherein the processing device further causes the radiation delivery system to:

generate a three-dimensional model using a plurality of two-dimensional images captured using the kV imaging beam.

15. The non-transitory computer-readable storage medium of claim 13, wherein the processing device further causes the radiation delivery system to:

generate a two-dimensional projection using the kV imaging beam.

16. The non-transitory computer-readable storage medium of claim 13, wherein the electromagnetic waves generated by the microwave source are dynamically adjusted by the energy adjuster during a treatment session.

* * * * *